(12) United States Patent
Corradi

(10) Patent No.: US 7,897,827 B2
(45) Date of Patent: Mar. 1, 2011

(54) PROPYLENE RECOVERY DURING REGENERATION OF AN OXYGENATE REMOVAL UNIT

(75) Inventor: Jason T. Corradi, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 604 days.

(21) Appl. No.: 12/001,432

(22) Filed: Dec. 11, 2007

(65) Prior Publication Data

US 2009/0149687 A1 Jun. 11, 2009

(51) Int. Cl.
*C07C 7/12* (2006.01)

(52) U.S. Cl. .............. 585/809; 585/639; 585/640; 585/807; 585/820; 585/822; 585/823; 585/824; 585/826; 585/833; 502/20; 502/34; 210/663

(58) Field of Classification Search .......... 502/20, 502/34; 585/640, 809, 822, 639, 807, 820, 585/823, 824, 826, 833; 210/663
See application file for complete search history.

(56) References Cited

U.S. PATENT DOCUMENTS

| | | | | |
|---|---|---|---|---|
| 5,177,298 A | * | 1/1993 | Yon et al. | 585/824 |
| 6,764,602 B2 | * | 7/2004 | Shutt et al. | 210/663 |
| 6,838,587 B2 | * | 1/2005 | Lattner et al. | 585/807 |

* cited by examiner

*Primary Examiner*—Prem C Singh
(74) *Attorney, Agent, or Firm*—Arthur E Gooding

(57) ABSTRACT

Processes and systems are disclosed that relate to the removal of impurities and separation the light olefins from an MTO product vapor stream. Specifically, the processes and systems relate to recovery of light olefins during regeneration of an adsorber in an oxygenate removal unit. Processes and systems for recovering light olefins during regeneration of an adsorber in an oxygenate removal unit can include recycling residual effluent stream to an upstream operation unit upstream of the oxygenate removal unit. Processes and systems for recovering light olefins during regeneration of an adsorber in an oxygenate removal unit can also include recycling residual effluent gas produced by depressurizing residual effluent in the first adsorber, as well as preferably venting an effluent gas from the first adsorber to a compressor upstream of the oxygenate removal unit.

16 Claims, 2 Drawing Sheets

PROPYLENE RECOVERY DURING REGENERATION OF AN OXYGENATE REMOVAL UNIT

TECHNICAL FIELD

The processes and systems disclosed herein relate to the treatment of product streams from methanol to olefin (MTO) processes. More particularly, the processes and systems disclosed herein relate to the removal of impurities and separation the light olefins, such as propylene, from an MTO product vapor stream.

BACKGROUND

Light olefins and other related hydrocarbons serve as feeds for the production of numerous chemicals. Light olefins have traditionally been produced from petroleum sources. However, oxygenates such as alcohols, particularly methanol, ethanol, and higher alcohols or their derivatives, are used as alternative materials for light olefin production. These alcohols may be produced by fermentation or from synthesis gas. Oxygenates are particularly attractive because they can be produced from such widely available materials as coal, natural gas, recycled plastics, various carbon waste streams from industry and various products and by-products from the agricultural industry.

Although many oxygenates have been discussed in the prior art, the principal focus on producing the desired light olefins has been on methanol conversion technology, primarily because of the availability of commercially proven methanol synthesis technology. Various methanol to olefin (MTO) procedures for catalytically converting methanol into the desired light olefin products have been developed.

The product vapor stream from MTO process is generally a raw product stream containing impurities. For example, a product vapor stream from an MTO process typically contains light olefins, oxygenates, and water. The product vapor stream undergoes a process to remove the impurities and separate the light olefins.

SUMMARY

The processes and systems disclosed herein relate to the removal of impurities and separation the light olefins from an MTO product vapor stream. Specifically, the processes and systems disclosed herein relate to recovery of light olefins during regeneration of an adsorber in an oxygenate removal unit.

In one aspect, a process is provided for recovering light olefins during regeneration of an adsorber in an oxygenate removal unit comprising: (a) providing an oxygenate removal unit comprising a plurality of adsorbers, wherein each adsorber comprises a feed end and an effluent end; (b) passing a liquid hydrocarbon feedstock to the feed end of at least a first adsorber and removing an effluent stream from the effluent end of the first adsorber; (c) isolating the first adsorber for regeneration by terminating passage of the liquid hydrocarbon feedstock to the feed end of the adsorber; (d) removing substantially all of the effluent stream from the first adsorber; (e) transferring substantially all of the removed effluent stream to a second adsorber; and (f) recycling residual effluent stream to an upstream operation unit upstream of the oxygenate removal unit.

In another aspect, a process is provided for recovering light olefins during regeneration of an adsorber in an oxygenate removal unit comprising: (a) providing an oxygenate removal unit comprising a plurality of adsorbers, wherein each adsorber comprises a feed end and an effluent end; (b) passing a liquid hydrocarbon feedstock to the feed end of at least a first adsorber and removing an effluent stream from the effluent end of the first adsorber; (c) isolating the first adsorber for regeneration by terminating passage of the liquid hydrocarbon feedstock to the feed end of the adsorber; (d) removing substantially all of the effluent stream from the first adsorber; (e) transferring substantially all of the removed effluent stream to a second adsorber; (f) depressurizing the first adsorber and any residual effluent remaining in the first adsorber; (g) recycling residual effluent gas produced by depressurizing residual effluent in the first adsorber; and (h) venting an effluent gas from the first adsorber to a compressor upstream of the oxygenate removal unit.

In a third aspect, a system is provided for recovering light olefins during regeneration of an adsorber in an oxygenate removal unit comprising: (a) a depropanizer upstream of an oxygenate removal unit; (b) an oxygenate removal unit comprising a plurality of adsorbers, wherein each adsorber comprises a feed end and an effluent end; (c) a supply of a liquid hydrocarbon feedstock that is fed to the feed end of at least a first adsorber; (d) a device that isolates the first adsorber from the system by terminating passage of the liquid hydrocarbon feedstock to the feed end of the first adsorber; (e) a transfer line operatively connected to the effluent end of the first adsorber that provides for removal of an effluent stream from the effluent end of the first adsorber and transfers substantially all of the removed effluent stream to a second adsorber; (f) a second adsorber that receives substantially all of the effluent stream from the first adsorber when the first adsorber is isolated for regeneration; (g) a recycle line that transfers residual effluent stream to an upstream operation unit.

DETAILED DESCRIPTION

Figure 1:
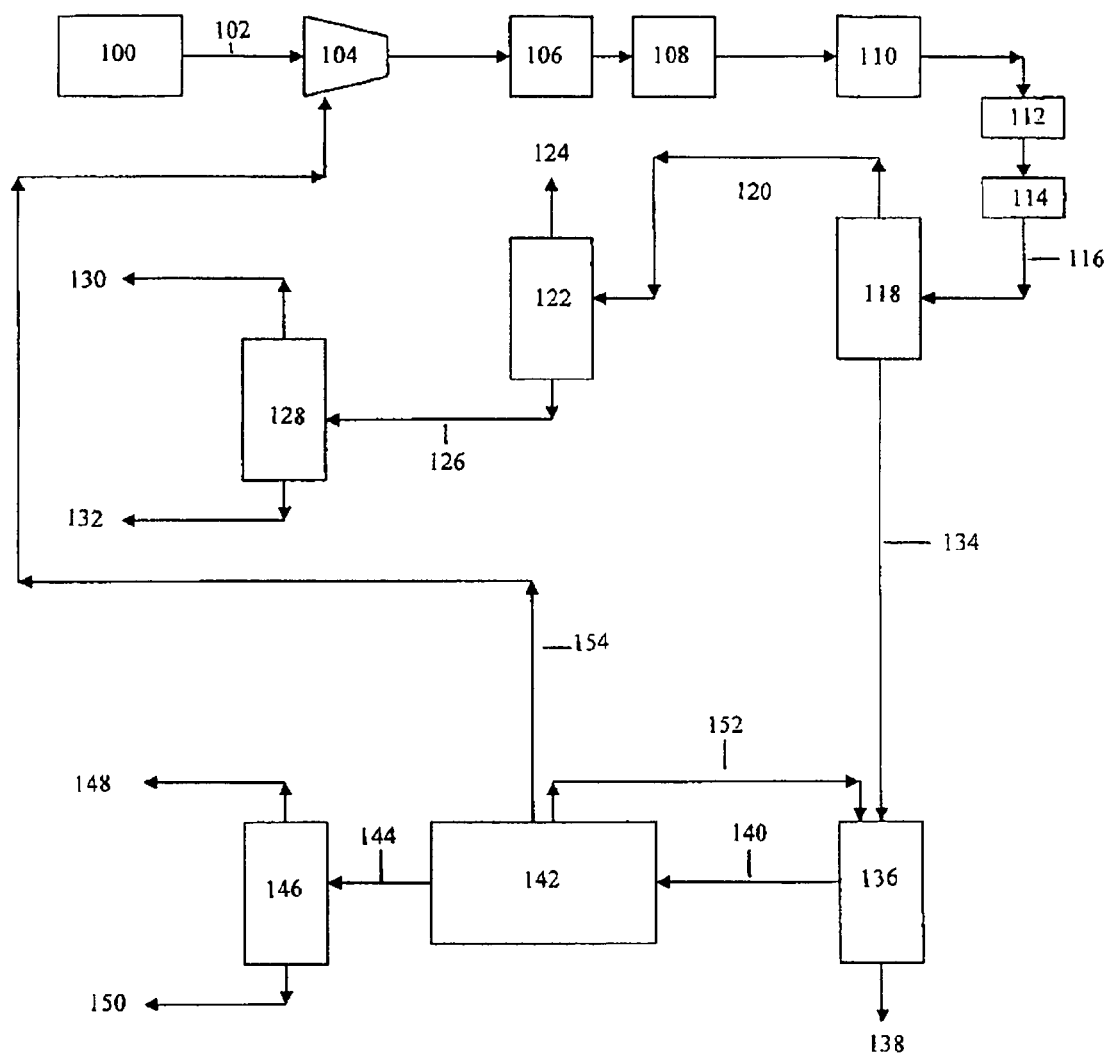
FIG. 1 is a flowchart illustrating a representative system for the removal of impurities and the separation of light olefins from an MTO product vapor stream.

One example of a process for the removal of impurities and the separation of light olefins from an MTO product vapor stream is illustrated in FIG. 1. An MTO product vapor stream typically contains light olefins, oxygenates, and water. For example, an MTO product vapor stream can contain unreacted methanol, dimethyl ether intermediate, ethylene, propylene, $C_4$ to $C_6$ olefins, and minor amounts of other hydrocarbons and oxygenates. Upon exiting an MTO reactor, the MTO product vapor stream will typically be at a relatively high temperature such as, for example, from about 350° C. to about 600° C. (about 660° F. to about 1110° F.). The MTO product vapor will then typically be cooled to about 37° C. (100° F.) to condense ad remove water byproduct. As illustrated, the product vapor stream 102 from the MTO process goes from the MTO process 100 to a compressor 104. The product vapor stream undergoes compression in the compressor 104, and the pressure of the vapor stream is increased. In at least some instances, liquid can be formed during compression, and is recycled upstream in the MTO process (not shown). The vapor stream exits the compressor 104 at increased pressure, and goes to an oxygenate absorber 106 and a scrubber 108. In the absorber 106, the vapor stream is contacted with a solvent such as, for example, water, to remove at least some oxygenates. In the scrubber 108, the vapor stream undergoes caustic scrubbing for bulk removal of carbon dioxide.

After undergoing caustic scrubbing, the vapor stream goes to a dryer 110, where moisture is removed from the vapor stream. The dried vapor stream then undergoes cooling 112 and is put through a distillation sequence 114 that results in the vapor stream becoming a liquid hydrocarbon feedstock 116. As further illustrated in FIG. 1, the liquid hydrocarbon feedstock goes to a deethanizer 118, which separates the $C_1$ and $C_2$ hydrocarbons from the hydrocarbons comprising $C_3$ or greater.

The $C_1$ and $C_2$ hydrocarbon feedstock 120 is sent from the deethanizer 118 to a demethanizer 122, where methane ($C_1$) 124 and other light impurities are removed. The resulting $C_2$ hydrocarbon feedstock 126 then goes to a $C_2$ splitter 128 that separates out ethylene 130 and ethane 132.

The feedstock 134 containing $C_3$ or greater olefins is sent from the deethanizer 118 to a depropanizer 136, where the $C_3$ fraction is removed from the remaining hydrocarbon feedstock 138 containing $C_4$ or greater olefins. The hydrocarbon feedstock 140 containing $C_3$ olefins goes to an oxygenate removal unit (ORU) 142. The oxygenate removal unit removes oxygenates such as, for example, dimethyl ether. The resulting product stream 144, sometimes referred to herein as the "effluent stream," goes to a $C_3$ splitter 146, where propylene 148 and propane are separated 150.

Figure 2:
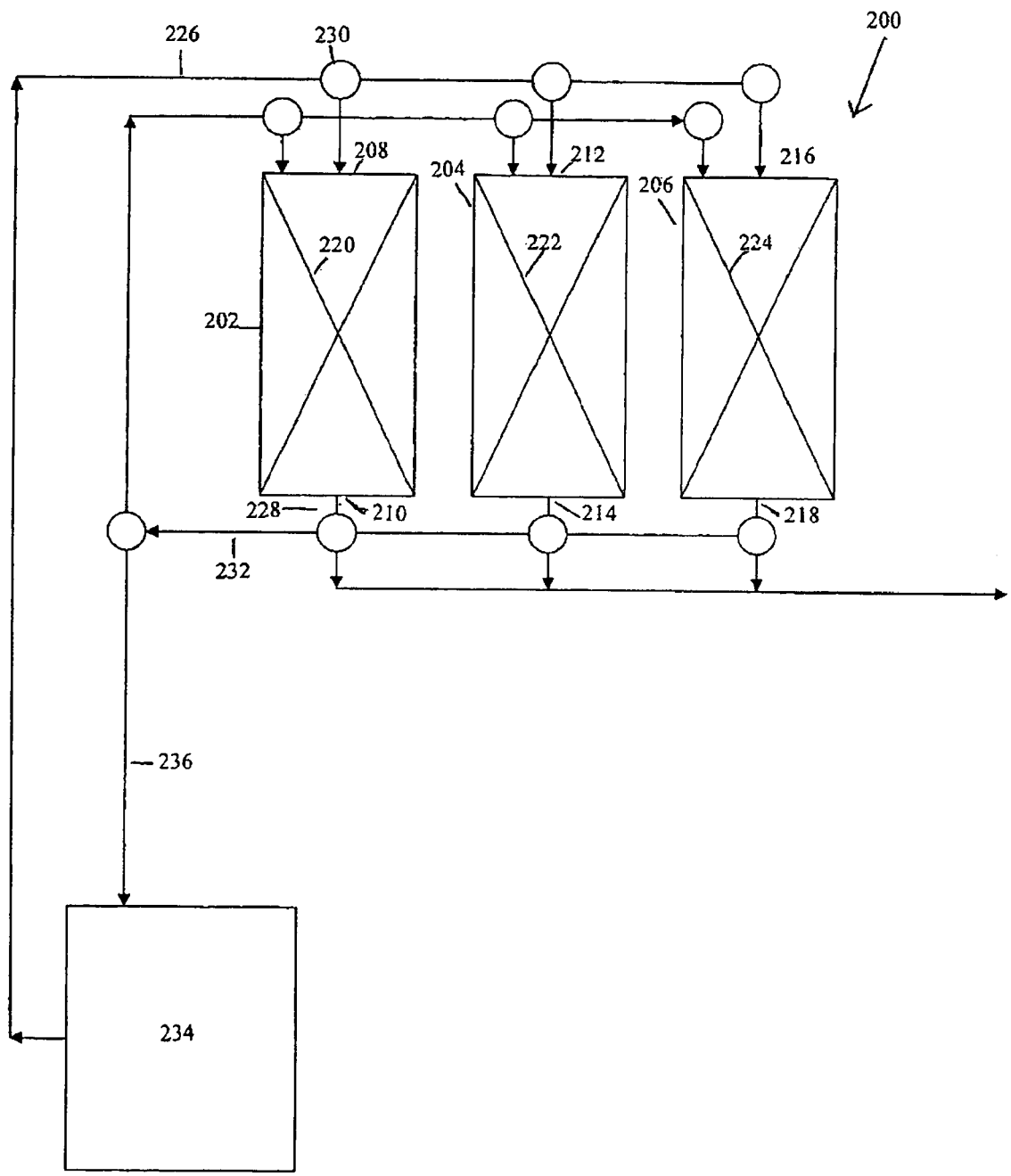
FIG. 2 is a representative system for recovering light olefins during regeneration of an adsorber in an oxygenate removal unit.

In some processes and systems, the oxygenate removal unit (ORU) utilizes a plurality of adsorbers to remove oxygenates. FIG. 2 illustrates a particularly preferred system for recovering light olefins during regeneration of an adsorber in an oxygenate removal unit in accordance with the process described above. As illustrated in FIG. 2, the ORU 200 has a first adsorber 202, a second adsorber 204, and a third adsorber 206. Each adsorber has a feed end and an effluent end. For example, as illustrated in FIG. 2, adsorber 202 has feed end 208 and effluent end 210, adsorber 204 has feed end 212 and effluent end 214, and adsorber 206 has feed end 216 and effluent end 218. Additionally, each adsorber includes an adsorbent bed that contains a solid adsorbent capable of selectively adsorbing trace amounts of oxygenates. For example, the first adsorber 202 has adsorber bed 220, the second adsorber 204 has adsorber bed 222, and the third adsorber 206 has adsorber bed 224. A supply of a liquid hydrocarbon feedstock that is fed to the feed end of at least a first adsorber. As illustrated in FIG. 2, a feedstock line 226 feeds the liquid hydrocarbon feedstock to the feed end of each of the adsorbers. An effluent stream is removed from the effluent end of at least the first adsorber through outlet piping 228. In preferred processes and systems, the liquid hydrocarbon feedstock is a product stream from an MTO process that contains propylene.

Adsorbers require regular, independent regeneration. Regeneration of a first adsorber can begin by isolating the first adsorber 202 for regeneration by terminating passage of the liquid hydrocarbon feedstock 226 to the feed end 208 of the adsorber. There is a device 230 that isolates the first adsorber from the system by terminating passage of the liquid hydrocarbon feedstock to the feed end of the first adsorber. The device 230 may be a valve that can be closed to prevent the flow of liquid hydrocarbon feedstock into the first adsorber. Preferably, the first adsorber 202 is then drained by removing substantially all of the effluent stream from the first adsorber and transferring substantially all of the removed effluent stream to another adsorber through a transfer line 232. The adsorber to which substantially all of the removed effluent stream is transferred can be, for example, the second adsorber 204, or the third adsorber 206. For example, as illustrated in FIG. 2, there is a transfer line 232 operatively connected to the effluent end 210 of the first adsorber that provides for removal of an effluent stream from the effluent end of the first adsorber 202, and can transfer substantially all of the removed effluent stream to the second adsorber 204. The second adsorber 204 can thus receive substantially all of the effluent stream from the first adsorber 202 when the first adsorber 202 is isolated for regeneration. The term "substantially all" is used in this context to indicate that a residual amount of effluent stream tends to remain within the first adsorber, as well as within the outlet piping at the effluent end of the first adsorber. The adsorber to which the effluent stream is transferred is preferably an adsorber that has undergone regeneration immediately prior to receiving the effluent stream from the first adsorber 202, and is in the process of coming back on-stream. The effluent stream from the first adsorber 202 is preferably used to fill the adsorber coming back on-stream prior to re-initiating the flow of hydrocarbon feedstock the adsorber coming back on-stream.

After the removal of substantially all of the effluent stream from the first adsorber, it is preferred that at least some of the residual effluent stream be recycled to an upstream operation unit 234 that is upstream of the oxygenate removal unit. This recycling can be done, for example, by passing residual effluent stream in a line 236 connected between at least the first and second adsorbers, and preferably connected between all of the adsorbers, to the upstream operation unit 234. In this manner, valuable hydrocarbon containing effluent stream can be recycled into the system, rather than being purged from the system as it might be otherwise. In the system illustrated in FIG. 1, for example, where the effluent stream, and thus the residual effluent stream, contains propylene, it is preferred that the upstream operation unit be a depropanizer. As illustrated in FIG. 1, a recycle line passes the residual effluent stream 152 from the ORU 142 to the depropanizer 136.

In at least some instances, a high pressure gas is passed through the first adsorber in the step of removing substantially all of the effluent stream from the first adsorber. The high pressure gas is preferably desulfurized natural gas, but can be other suitable gasses. The high pressure gas can be utilized to provide the pressure that passes residual effluent stream to the upstream operation unit in order to recycle it. This is believed to be particularly effective in recycling residual effluent stream that remains in the outlet piping at the effluent end of the adsorber.

When a high pressure gas is utilized in removing substantially all of the effluent stream from the first adsorber, the process of regenerating the adsorber preferably includes depressurizing the adsorber and any residual effluent remaining in the first adsorber. Accordingly, there is preferably a depressurization gas that depressurizes the first adsorber and any residual effluent remaining in the first adsorber. When residual effluent stream remaining in the adsorber is depressurized, it is believed that it will change from being in a liquid state to being in a vapor state, and thus become a residual effluent gas.

It is preferred that residual effluent gas produced by depressurizing residual effluent in the first adsorber be recycled. Recycling of residual effluent gas can be accomplished, for example, by venting effluent gas from the adsorber undergoing regeneration such as, for example, the first adsorber, to a compressor upstream of the oxygenate removal unit. Thus, in preferred systems, there is a venting line for recycling residual effluent gas produced by depressurizing residual effluent in the first adsorber. The venting line transfers residual effluent gas to a compressor upstream of the oxygenate removal unit. Such a compressor can be, for example, an MTO product compressor. In the system illustrated in FIG. 1, for example, residual effluent gas 154 is passed through a line, or lines, to compressor 104.

After the effluent stream has been removed from the adsorber, and, in preferred processes, after the adsorber has been depressurized, the adsorber can be regenerated with a regeneration gas. Nitrogen is a preferred regeneration gas. More preferably, the regeneration gas is nitrogen that is heated to about 287° C. (550° F.). In preferred processes, the regeneration gas is passed to the adsorbent bed of the first adsorber at a temperature effective to desorb oxygenates from the solid adsorbent and recover the oxygenates from the first adsorbent bed in a spent regenerant vapor stream. Preferably, the regenerated first adsorber is then filled with effluent stream that has been removed from another adsorber that is beginning to undergo regeneration as described herein with respect to the first adsorber.

From the foregoing, it will be appreciated that although specific representative structures and processes have been described herein for purposes of illustration, various modifications may be made without deviating from the spirit or scope of the disclosure. It is therefore intended that the foregoing detailed description be regarded as illustrative rather than limiting, and that it be understood that it is the following claims, including all equivalents, that are intended to particularly point out and distinctly claim the disclosure subject matter.

What is claimed is:

1. A process for recovering light olefins during regeneration of an adsorber in an oxygenate removal unit comprising:
   (a) providing an oxygenate removal unit comprising a plurality of adsorbers, wherein each adsorber comprises a feed end and an effluent end;
   (b) passing a liquid hydrocarbon feedstock comprising said light olefins to the feed end of at least a first adsorber and removing a product effluent stream from the effluent end of the first adsorber;
   (c) passing the product effluent stream to a propane/propylene splitter, thereby creating a propylene stream;
   (d) isolating the first adsorber for regeneration by terminating passage of the liquid hydrocarbon feedstock to the feed end of the adsorber;
   (e) removing substantially all of the product effluent stream from the first adsorber and transferring to a second adsorber;
   (f) regenerating the first adsorber and creating a residual effluent stream; and
   (g) recycling the residual effluent stream to a unit upstream of the oxygenate removal unit.

2. The process of claim 1, wherein the step of (g) recycling comprises passing residual effluent stream in a line(s) connected between at least the first and second adsorbers to the upstream operation unit.

3. The process of claim 1, wherein the effluent stream comprises propylene, and wherein the upstream operation unit is a depropanizer.

4. The process of claim 1, further comprising the step of (f) depressurizing the first adsorber.

5. The process of claim 4, wherein the step of (f) depressurizing the first adsorber comprises venting an effluent gas to a compressor upstream of the oxygenate removal unit.

6. The process of claim 5, wherein the compressor is an MTO product compressor.

7. The process of claim 1, further comprising the step of regenerating the first adsorber with nitrogen.

8. The process of claim 1, wherein the liquid hydrocarbon feedstock is a product stream from an MTO process comprising propylene.

9. The process of claim 1, wherein a high pressure gas is passed through the first adsorber in the step of (e) removing.

10. The process of claim 9, wherein the high pressure gas is desulfurized natural gas.

11. The process of claim 1, wherein the second adsorber has undergone regeneration immediately prior to receiving the effluent stream from the first adsorber.

12. A process for recovering light olefins during regeneration of an adsorber in an oxygenate removal unit comprising:
   (a) providing an oxygenate removal unit comprising a plurality of adsorbers, wherein each adsorber comprises a feed end and an effluent end;
   (b) passing a liquid hydrocarbon feedstock comprising said light olefins to the feed end of at least a first adsorber and removing a product effluent stream from the effluent end of the first adsorber;
   (c) passing the product effluent stream to a propane/propylene splitter, thereby creating a propylene stream;
   (d) isolating the first adsorber for regeneration by terminating passage of the liquid hydrocarbon feedstock to the feed end of the adsorber;
   (e) removing substantially all of the product effluent stream from the first adsorber and transferring to a second adsorber;
   (f) depressurizing the first adsorber and any residual effluent remaining in the first adsorber, and creating a residual effluent gas; and
   (g) recycling the residual effluent gas produced by depressurizing residual effluent in the first adsorber.

13. The process of claim 12, wherein the step of (g) recycling comprises venting an effluent gas from the first adsorber to a compressor upstream of the oxygenate removal unit.

14. The process of claim 12, further comprising recycling residual effluent stream to a an upstream operation unit upstream of the oxygenate removal unit prior to depressurizing the first adsorber.

15. The process of claim 14, wherein the recycling comprises passing residual effluent stream in a line(s) connected between at least the first and second adsorbers to the upstream operation unit.

16. The process of claim 15, wherein the residual effluent stream comprises propylene, and wherein the upstream operation unit is a depropanizer.

* * * * *